(12) United States Patent
Becker (10) Patent No.: US 9,469,588 B2
(45) Date of Patent: Oct. 18, 2016

(54) ALKYLATING PROCESS

(71) Applicant: ExxonMobil Chemical Patents Inc., Baytown, TX (US)

(72) Inventor: Christopher L. Becker, Manhattan, KS (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/442,292

(22) PCT Filed: Dec. 6, 2013

(86) PCT No.: PCT/US2013/073689
§ 371 (c)(1),
(2) Date: May 12, 2015

(87) PCT Pub. No.: WO2014/093177
PCT Pub. Date: Jun. 19, 2014

(65) Prior Publication Data
US 2016/0237013 A1    Aug. 18, 2016

Related U.S. Application Data

(60) Provisional application No. 61/736,581, filed on Dec. 13, 2012.

(30) Foreign Application Priority Data

Mar. 19, 2013    (EP) ..................................... 13159865

(51) Int. Cl.
*C07C 45/53* (2006.01)
*C07C 37/08* (2006.01)
*C07C 2/74* (2006.01)
*C07C 409/14* (2006.01)

(52) U.S. Cl.
CPC .................. *C07C 45/53* (2013.01); *C07C 2/74* (2013.01); *C07C 37/08* (2013.01); *C07C 409/14* (2013.01); *C07C 2101/14* (2013.01); *C07C 2529/72* (2013.01)

(58) Field of Classification Search
CPC .......... C07C 45/53; C07C 37/08; C07C 2/74
USPC .......................... 568/346, 347, 798; 585/467
See application file for complete search history.

(56) References Cited

U.S. PATENT DOCUMENTS

| 3,112,256 A | 11/1963 | Young et al. |
| 6,037,513 A | 3/2000 | Chang et al. |

FOREIGN PATENT DOCUMENTS

| WO | WO 2009/128984 | 10/2009 |
| WO | WO 2012/024026 | 2/2012 |

*Primary Examiner* — Sikarl Witherspoon
(74) *Attorney, Agent, or Firm* — Siwen Chen; Stephen A. Baehl (57) ABSTRACT

An alkylating process such as hydroalkylating process comprising feeding a gas material and a liquid material into the reactor, distributing the liquid material to the upper surface of a bed of a catalyst substantially uniformly. The substantial uniform distribution of the liquid material to the upper surface allows for substantially uniform distribution of liquid reaction medium in the bed, thereby preventing hot spot and undesirable continuous liquid zone, both of which can cause the production of undesired by-products. The invention is particularly useful for the hydroalkylation reaction of benzene in making cyclohexylbenzene, which can be used for making cyclohexanone and phenol.

25 Claims, 1 Drawing Sheet

ALKYLATING PROCESS

PRIORITY CLAIM TO RELATED APPLICATIONS

This application is a National Stage Application of International Application No. PCT/US2013/073689 filed Dec. 6, 2013, which claims priority to U.S. Provisional Application Ser. No. 61/736,581 filed Dec. 13, 2012, and European Application No. 13159865.8 filed Mar. 19, 2013, the disclosures of which are fully incorporated herein by their reference.

FIELD

The present invention relates to a process for alkylating an aromatic compound. In particular, the present invention relates to a process for alkylating an aromatic compound using a liquid feed and a gas feed. The present invention is useful, e.g., in making cyclohexylbenzene via the hydroalkylation of benzene.

BACKGROUND

Phenol and cyclohexanone are important materials in the chemical industry and are useful in, for example, the production of phenolic resins, bisphenol A, $\epsilon$-caprolactam, adipic acid, and plasticizers.

Currently, a common route for the production of phenol is the Hock process. This is a three-step process in which the first step involves alkylation of benzene with propylene to produce cumene, followed by oxidation of the cumene to the corresponding hydroperoxide, and then cleavage of the hydroperoxide to produce equimolar amounts of phenol and acetone. However, the world demand for phenol is growing more rapidly than that for acetone. In addition, due to a developing shortage, the cost of propylene is likely to increase.

Thus, a process that uses higher alkenes instead of propylene as feed and coproduces higher ketones, such as cyclohexanone, rather than acetone may be an attractive alternative route to the production of phenols. For example, there is a growing market for cyclohexanone, which is used as an industrial solvent, as an activator in oxidation reactions, and in the production of adipic acid, cyclohexanone resins, cyclohexanone oxime, caprolactam, and nylon 6.

It is known from, e.g., U.S. Pat. No. 6,037,513 that cyclohexylbenzene can be produced by contacting benzene with hydrogen in the presence of a bifunctional catalyst comprising a molecular sieve of the MCM-22 type and at least one hydrogenation metal selected from palladium, ruthenium, nickel, cobalt, and mixtures thereof. The contacting is conducted at a temperature of about 50° C. to 350° C., a pressure of about 100 kPa to 7000 kPa, a benzene to hydrogen molar ratio of about 0.01 to 100, and a WHSV of about 0.01 to 100. In addition to cyclohexylbenzene, the effluent of the hydroalkylation reaction comprises cyclohexane, dicyclohexylbenzene, bicyclohexane, and a significant amount of benzene. This reference also discloses that the resultant cyclohexylbenzene can be oxidized to the corresponding hydroperoxide which is then decomposed to the desired phenol and cyclohexanone co-product.

SUMMARY

The highly exothermic hydroalkylation reaction of benzene over an acid catalyst, such as MCM-22, is typically conducted with at least part of the benzene in liquid phase. The flow of the liquid in the catalyst bed functions in part to cool the catalyst and the reactor. It has been found that if a relatively dry pocket due to insufficient flowing liquid forms, hot spot may be created as a result of the oversupply of hydrogen relative to benzene, leading to undesirable side reactions and production of unwanted by-products. On the other hand, in the case of oversupply of liquid and the formation of a continuous liquid area, by-products such as biphenyl can be generated due to hydrogen depletion. As such, an even distribution of liquid benzene in the catalyst bed is highly desirable in the hydroalkylation reactor. In other alkylating processes involving an exothermic reaction between a gas phase and a liquid phase on the surface of a solid catalyst, there is a similar need of controlling temperature and feed concentration gradient inside the catalyst bed.

The present invention addresses the above issues and need by, e.g., using a fluid distributing device between an inlet of the liquid material feed and the catalyst bed.

A first aspect of the present disclosure relates to a process for making cyclohexylbenzene, the process comprising:

(1A) feeding a gas material comprising hydrogen gas and a liquid material comprising benzene into a hydroalkylation reactor;

(1B) distributing the liquid material to the upper surface of a bed of a solid hydroalkylating catalyst inside the hydroalkylation reactor such that in any given continuous area of 10.0 centimeters by 10.0 centimeters inside a first horizontal cross-section of the bed 1.0 centimeter below the upper surface of the bed, the average quantity of liquid benzene passing through the given continuous area per second $Qbz0$ is in a range from 60% to 140% of $Qbz1$, where $Qbz1$ is the average quantity of liquid benzene passing through the whole first horizontal cross-section, expressed in terms of quantity of liquid benzene per 100 square centimeters per second; and (1C) contacting liquid benzene and hydrogen gas with the catalyst under hydroalkylation conditions to produce a hydroalkylation reaction effluent comprising cyclohexylbenzene.

A second aspect of the present disclosure relates to a process for making phenol and/or cyclohexanone, the process comprising:

(2A) producing cyclohexylbenzene according to the process of the first aspect of the present disclosure;

(2B) oxidizing at least a portion of the cyclohexylbenzene to obtain an oxidation reaction product comprising of cyclohexylbenzene hydroperoxide; and (2C) cleaving at least part of the cyclohexylbenzene hydroperoxide to obtain a cleavage effluent comprising phenol and cyclohexanone.

A third aspect of the present disclosure relates to a process for alkylating an aromatic compound, the process comprising:

(3A) feeding a gas material and a liquid material comprising the aromatic compound into an alkylation reactor;

(3B) distributing the liquid material to an upper surface of a bed of a solid catalyst inside the reactor such that in any given continuous area of 10.0 centimeters by 10.0 centimeters within a first horizontal cross-section of the bed 1.0 centimeter below the upper surface, the quantity of the liquid material passing through the given continuous area per second is in a range from 60% to 140% of the average quantity of the liquid material passing through the whole first horizontal cross-section, expressed in terms of quantity of the liquid material per 100 square centimeters per second; and (3C) contacting the liquid material and the gas material with the catalyst under alkylating conditions to produce an alkylation reaction effluent comprising an alkyl-substituted aromatic compound.

The processes of the present disclosure can have the following advantages. First, by using a fluid distributing device between the liquid feed inlet of the reactor and the upper surface of a solid catalyst bed inside the reactor, one can achieve a substantially uniform distribution of the liquid (e.g., benzene) on the upper surface of the bed, and accordingly a substantially uniform distribution of the liquid through the bed, hence a substantially uniform gas (e.g., hydrogen) to liquid molar ratio in the reactor. Second, the substantially uniform distribution of gas to liquid ratio in the reactor can prevent (i) the formation of hot pocket in the reactor and the hence the production of undesirably high level of some by-products (e.g., cyclohexane) and (ii) the formation of continuous liquid zone with depleted hydrogen and hence the production of undesirably high level of other by-products (e.g., biphenyl). Third, the substantially uniform distribution of gas to liquid molar ratio in the reactor can also prevent the formation of intermediates prone to coking and deactivating the alkylating catalyst. Thus, the processes of the present disclosure are particularly advantageous for pure alkylation reaction and hydroalkylation alike involving feeding a liquid and a gas reactant into the reactor.

Additional features and advantages of the invention will be set forth in the detailed description and claims, as well as the appended drawings. It is to be understood that the foregoing general description and the following detailed description are merely exemplary of the invention, and are intended to provide an overview or framework to understanding the nature and character of the invention as it is claimed.

DETAILED DESCRIPTION

In the present disclosure, a process is described as comprising at least one "step." It should be understood that each step is an action or operation that may be conducted once or multiple times in the process, in a continuous or discontinuous fashion. Unless specified to the contrary or the context clearly indicates otherwise, each step in a process may be conducted sequentially in the order as they are listed, with or without overlapping with one or more other step, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be conducted simultaneously with respect to an intermediate material resulting from treating the raw materials fed into the process at an earlier time in the first step. Preferably, the steps are carried out in the order listed.

Unless otherwise indicated, all numbers indicating quantities in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a hydrogenation metal" include embodiments where one, two or more different types of the hydrogenation metals are used, unless specified to the contrary or the context clearly indicates that only one type of the hydrogenation metal is used.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question unless specified or indicated otherwise. All ranges expressed herein should include both end points as two specific embodiments unless specified or indicated to the contrary.

The terms "group," "radical," and "substituent" are used interchangeably in the present disclosure.

As used herein, the generic term "dicylcohexylbenzene" includes, in the aggregate, 1,2-dicyclohexylbenzene, 1,3-dicylohexylbenzene, and 1,4-dicyclohexylbenzene, unless clearly specified to mean only one or two thereof. The term cyclohexylbenzene, when used in singular form, means mono substituted cyclohexylbenzene.

As used herein, the term "horizontal" means substantially perpendicular to the gravity vector. Thus, a horizontal cross-section is a planar cross-section substantially normal to the gravity vector. A horizontal cross-section in the present disclosure may deviate from a reference plane strictly perpendicular to the gravity vector by, e.g., at most A°, where A can be, e.g., 15, 14, 13, 12, 11, 10, 9, 8, 7, 6, 5, 4, 3, 2, or 1.

As used herein, the distance from a cross-section to the upper surface of the bed is the shortest distance between them, to the extent the upper surface may be planar or curved.

Generally, in the present disclosure, a substantially uniform distribution of a gas or liquid material across a cross-section is defined as: in any given continuous area of 10.0 centimeters by 10.0 centimeters inside the given cross-section, the average quantity of the gas or liquid material passing through the given continuous area per second, Qty0, is in a range from 60% to 140% of Qty1, where Qty1 is the average quantity of the gas or liquid material passing through the whole cross-section, expressed in terms of quantity of the material per 100 square centimeters per second. The actual Qty0 can range from a1*Qty1 to a2*Qty1, where a1 can be, e.g., 0.60, 0.65, 0.70, 0.75, 0.80, 0.85, 0.90, 0.95, 0.98, and 0.99, and a2 can be 1.40, 1.35, 1.30, 1.25, 1.20, 1.15, 1.10, 1.05, 1.02, and 1.01. The calculation of Qty1 can be conducted according to the following equation: Qty1=Qty2*100/A, where Qty2 is the total amount of the gas or liquid material passing through the whole given horizontal cross-section per second, and A is the total area of the whole given cross-section.

The term "MCM-22 type material" (or "material of the MCM-22 type" or "molecular sieve of the MCM-22 type" or "MCM-22 type zeolite"), as used herein, includes one or more of:

molecular sieves made from a common first degree crystalline building block unit cell, which unit cell has the MWW framework topology. A unit cell is a spatial arrangement of atoms which if tiled in three-dimensional space describes the crystal structure. Such crystal structures are discussed in the "Atlas of Zeolite Framework Types," Fifth Edition, 2001, the entire content of which is incorporated as reference;

molecular sieves made from a common second degree building block, being a 2-dimensional tiling of such MWW framework topology unit cells, forming a monolayer of one unit cell thickness, desirably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 type include those molecular sieves having an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques such as using the K-alpha doublet of copper as incident radiation and a diffractometer equipped with a scintillation counter and associated computer as the collection system.

Materials of the MCM-22 type include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), and mixtures thereof. Other molecular sieves, such as UZM-8 (described in U.S. Pat. No. 6,756,030), may be used alone or together with the MCM-22 type molecular sieves as well for the purpose of the present disclosure. Desirably, the molecular sieve is selected from (a) MCM-49; (b) MCM-56; and (c) isotypes of MCM-49 and MCM-56, such as ITQ-2.

An alkylating process according to the present disclosure typically involves a gaseous phase, a liquid phase, and an alkylation reaction taking place in the presence of a solid phase catalyst. The process involves at least one reaction between the gas material and the liquid fed into the process, which may or may not be the alkylation reaction per se, as discussed below.

For example, in the case of the HOCK process for making cumene using a propylene gas feed and a benzene liquid feed, the following alkylation reaction occurs:

The alkylation reaction may occur between components in the gaseous phase and the liquid phase, such as in the above Reaction-1, or between components in the gaseous phase, or between components in the liquid phase. The alkylation reaction is facilitated by a bed of solid catalyst, such as a solid acid, e.g., a molecular sieve of the MCM-22 type. Other reactions in addition to alkylation, such as hydrogenation and dehydrogenation, may take place in the same reactor in the presence of a catalyst that is the same as, a part of or separate from the alkylation catalyst.

For another example, in the case of the hydroalkylation of benzene by hydrogen, a $H_2$-containing gas feed and a liquid benzene-containing liquid feed may be charged into the reactor, where the following reactions, among others, may take place on the surface of a bifunctional catalyst comprising a hydrogenating metal component such as Pd and a solid acid component such as a molecular sieve of the MCM-22 type:

(Reaction-6)

(Reaction-7)

(Reaction-8)

Thus, the gas material fed to the process may comprise $H_2$ and/or an olefin, and the liquid fed to the process may comprise an aromatic compound having the following general formula (F-I):

(F-I)

wherein $R^1$, the same or different at each occurrence, each independently represents a linear or cyclic alkyl having from 1-10 carbon atoms, and m is an integer from 0 to 5. Non-limiting examples of such aromatic compounds include: benzene, toluene, ethylbenzene, n-propylbenzene, cumene, n-butylbenzene, 2-phenylbutane, o-xylene, m-xylene, p-xylene, and the like. Where the gas material fed into the process comprises hydrogen, and the reaction involves a step of hydroalkylation, an olefin may be produced as an intermediate compound, which may become part of the liquid reaction medium in the reactor and react with the aromatic compound in the alkylation step. Thus, either or both of the gas material and the liquid material fed to the process of the present disclosure and/or the reaction medium in the reactor may comprise an olefin represented by the following general formula (F-II):

(F-II)

wherein $R^2$ and $R^3$ each independently represent hydrogen or an alkyl group having from 1 to 4 carbon atoms, or $R^2$ and $R^3$, defined above, are linked via a covalent bond to form together with the adjacent —CH=CH— linkage an optionally substituted cyclic group having from 4 to 10 carbon atoms. Non-limiting examples of the olefin that may be present in the gas material and/or the liquid material fed into the process and the reaction medium of the present disclosure include: ethylene, propylene, 1-butene, 2-butene, 2-methylpropylene, cyclohexene, methylcyclopentene, and the like.

It has been found that the molar ratio of the gas material (e.g., propylene or hydrogen) to the liquid material (e.g., benzene) fed into the reactor determines to what extent the above desired and undesired reactions take place on the catalyst. For example, in the case of hydroalkylation of benzene, where there is a substantial oversupply of $H_2$, more cyclohexane via Reaction-3 and bicyclohexylbenzene via Reaction-5 and Reaction-6 may be produced; and in the case of a substantial oversupply of benzene, more biphenyls via Reaction-8 may be produced. In a hydroalkylation reaction where the target product is cyclohexylbenzene, all byproducts cyclohexane, biphenyl, and bicyclohexane are undesired and should be minimized Therefore, the molar ratio of $H_2$ to benzene is desired to be within a given range in the feed materials, such as from RM1 to RM2, where RM1 can be 0.01, 0.05, 0.10, 0.15, 0.20, 0.25, 0.30, 0.35, 0.40, 0.45, 0.50, 0.60, 0.80, 1.00, and RM2 can be 15.0, 10.0, 8.0, 6.0, 4.0, 2.0, 1.0, 0.90, 0.80, 0.70, 0.60, as long as RM1<RM2.

The alkylation and hydroalkylation reactions may be conducted in a fixed-bed catalyst reactor, where the catalyst particles are stacked inside a column, and the gas and liquid materials are allowed to travel, e.g., in a direction from the top to bottom, in contact with the surface of the catalyst particles, whereby the hydrogenation and/or alkylation reactions take place. We have found that, even if the molar ratio of the gas material and liquid material in the feed material(s) are maintained substantially uniform at the feed inlet(s) throughout a reaction campaign, the local distributions of the liquid and/or gas phase in the catalyst bed can vary quite significantly across the catalyst bed from one side of the reactor to the other, and/or from the top to the bottom of the catalyst bed, if initial distribution of the liquid to the upper surface of the bed is not well controlled and non-uniform. For example, in one location, the supply of the liquid feed may be so low that a dry pocket forms. The lack of sufficient liquid flowing in the dry pocket results in inadequate cooling, hence the development of a hot spot and the formation of bicyclohexane and bi-cyclohexylbenzene therein. Simultaneously in another location, oversupply of the liquid feed may occur, resulting in the depletion of $H_2$ in the liquid reaction medium on the catalyst surface and the formation of more biphenyl than desired. Therefore, it is highly desirable that the liquid feed material is distributed substantially uniformly across the catalyst bed in a horizontal cross-section of the catalyst bed, and a substantially uniform H$_2$ to benzene molar ratio is achieved in the cross-section.

For example, a desired product in the reaction effluent of the alkylation process can be represented by the following general formula (F-III):

(F-III)

where:

R$^1$, the same or different at each occurrence, each independently represents a linear or cyclic alkyl having from 1-10 carbon atoms;

m is an integer from 0 to 5; and

R$^2$ and R$^3$ each independently represent hydrogen or an alkyl group having from 1 to 4 carbon atoms, or R$^2$ and R$^3$ are linked via a covalent bond to form together with the adjacent —CH—CH$_2$— linkage an optionally substituted cyclic group having from 4 to 10 carbon atoms.

Both the gas material and the liquid material can be fed into the reactor from a location above the bed of the catalyst, and the reaction effluent exits the reactor at a location in proximity to the bottom of the bed of the catalyst, such as a location below the bottom of the bed of the catalyst. The liquid and gas materials fed into the reactor can mix above the bed of the catalyst, then pass through the bed in the direction from the top to the bottom, and undergo the alkylation reaction and other reactions, if any, and eventually produce the reaction effluent which exits the reactor in proximity to the bottom of the reactor. The liquid material feed and the liquid reaction media inside the reactor flow downwards in part due to the effect of gravity, while the gas material stream flows as a result of pressure drop from the gas feed inlet to the gas effluent outlet. The reaction effluent may comprise both liquid and gas in a single stream or multiple streams, or mostly liquid in one or more stream(s) and mostly gas in one or more other stream(s). This liquid down-flow configuration is particularly advantageous for carrying out gas-liquid reaction on the surface of a solid catalyst bed and can allow for a substantially uniform distribution of both liquid and gas in a horizontal cross-section of the solid catalyst. In such reactors, the liquid is first dispensed onto the upper surface of the catalyst, then flows down the bed along the boundary of the catalyst particles, wet the surface of the catalyst particles in the bed along its way, and undergoes the desired reaction(s) such as alkylation. As mentioned above, a substantially uniform distribution of the liquid reaction media inside the bed of the catalyst is highly desired to control the amount of by-products produced inside the reactor. It was found that the distribution of the liquid fed into the reactor to the upper surface of the bed of the catalyst can significantly impact the distribution of the liquid reaction medium in the bulk of the bed of the catalyst. To achieve a substantially uniform distribution of the liquid reaction medium in the bulk, it is highly desired that the liquid fed into to the reactor is distributed substantially uniformly to the upper surface of the bed.

At least a portion of both of the gas material and the liquid material fed into the reactor can be supplied to the reactor at the same horizontal level of the reactor. Specifically, the gas material and the liquid material can be mixed and then fed into the reactor together via the same port(s). Alternatively, the gas material and the liquid material are fed into the reactor via different, separate ports. At least some of the ports through each of which the gas material and liquid are fed into the reactor are above the upper surface of the bed of the catalyst. To facilitate a substantially uniform distribution of the liquid feed material to the upper surface of the bed of the catalyst, a plurality of ports may be used above the upper surface of the bed, through each of which a portion of the total liquid feed is delivered into the reactor. Generally, it is easier to achieve a substantially uniform distribution of the gas material in the space above the upper surface of the bed of the catalyst than the liquid. Nonetheless, to ensure such uniform distribution of the gas material, multiple ports for feeding gas may be used above the upper surface of the bed of the catalyst as well.

It has been found that, in order to achieve a substantially uniform distribution of the liquid feed material in the space immediately above the upper surface of the bed of the catalyst, a fluid distributing device may be desired between the inlet of the liquid and the upper surface of the bed of the catalyst. Such fluid distributing device can receive the liquid material fed into the reactor through the inlet(s), redirect the flow thereof in multiple horizontal directions, and eventually deliver the liquid into the space above the upper surface of the bed in the form of liquid droplets. Desirably, such droplets have substantially uniform distribution of droplet size, and the distribution of the number of droplets in a horizontal cross-section of the internal space immediately above the upper surface of the bed is substantially uniform.

The fluid distributing device functions to distribute both the liquid and gas feed materials substantially uniformly to the bed of the catalyst, such that the distribution of the composition of the atmosphere inside the reactor in a space between a second horizontal cross-section of the internal space of the reactor 1.0 centimeter above the upper surface of the bed and a third horizontal cross-section of the internal space of the reactor 2.0 centimeters above the upper surface of the bed is substantially uniform.

The fluid distributing device can be a layer of inert material stacked in a space between the upper surface of the bed of the catalyst and the inlet(s) of the liquid and/or gas feed. Non-limiting examples of such inert material can be a metal mesh, glass beads, ceramic particles, and the like. Mechanical structures designed specifically for making liquid droplets with substantially even distribution thereof can be used as well. Non-limiting examples of such devices include the following models of liquid distributors supplied by Koch-Glitsch, LP, 4111 East 37$^{th}$ Street North, Wichita, Kans. 67220, United States: No. 106 pan distributor; No. 107 pan distributor; No. 116 deck distributor; No. 117 deck redistributor with bottom orifices; No. 126 channel distributor with bottom orifices; No. 127 channel redistributor with bottom orifices; No. 136 channel distributor with drip tubes; No. 137 channel redistributor with drip tubes; No. 141 tubular distributor; No. 156 through distributor with enhanced baffle plates; No. 186 through distributor with drip tubes; No. 905 pan distributor with V-notch risers; No. 906 pan distributor with bottom orifices; No. 916 deck distributor with bottom orifices; No. 926 channel distributor with bottom orifices; No. 976 through distributor with bottom orifices; No. 985 through distributor with weirs; No. 986 through distributor with tubes; No. 996 through distributor with drip point multipliers; No. 917 deck redistributor with bottom orifice; No. 927 channel distributor with bottom orifices; No. 941 pipe-arm distributor with orifices; No. 943 spray nozzle distributor; and No. 961 enclosed channel distributor.

As a result of the substantially uniform distribution of the liquid feed onto the upper surface of the bed of the catalyst, a substantially uniform distribution of the liquid feed (or liquid benzene or other specific component of the liquid feed) and/or the gas feed material (or hydrogen gas or other specific component of the gas feed material) at at least one of the following locations can be achieved:

the first horizontal cross-section 1.0 centimeter below the upper surface of the bed;
a horizontal cross-section 10.0 centimeters below the upper surface of the bed, if present;
a horizontal cross-section 20.0 centimeters below the upper surface of the bed, if present;
a horizontal cross-section 30.0 centimeters below the upper surface of the bed, if present;
a horizontal cross-section 40.0 centimeters below the upper surface of the bed, if present;
a horizontal cross-section 50.0 centimeters below the upper surface of the bed, if present;
a horizontal cross-section 80.0 centimeters below the upper surface of the bed, if present; and
a horizontal cross-section 100.0 centimeters below the upper surface of the bed, if present.

It is highly desirable that the bed of the catalyst is packed in the reactor such that the upper surface is flat and horizontal. It is further desirable that the horizontal cross-sections of the bed of the catalyst at different elevations maintain substantially the same geometry from the top to the bottom. To that extent, a cylindrical bed is highly desirable. Furthermore, it is highly desired that the density distribution of the catalytically active component(s) of the catalyst material packed in the bed is substantially uniform in any given horizontal cross-section, and remains substantially uniform from the top to the bottom of the bed. By "substantially uniform" here is meant that the distribution of the density of the catalytically active component is within a range of $a1*Dav$ to $a2*Dav$, in any given continuous area of 10.0 cm by 10.0 cm in a horizontal cross-section of the bed, where Dav is the average quantity of the active catalytic material across the whole cross-section expressed in terms of quantity per 100 $cm^2$, a1 can be 0.60, 0.65, 0.70, 0.75, 0.80, 0.85, 0.90, 0.95, 0.98, or 0.99, and a2 can be 1.40, 1.35, 1.30, 1.25, 1.20, 1.15, 1.10, 1.05, 1.02, or 1.01. As used herein, a "catalytically active component" is a component responsible for catalyzing the relevant reactions in the reactor. Thus, for a bed of hydroalkylation catalyst comprising Pd, $Al_2O_3$, and a MCM-22 type molecular sieve, the catalytically active components would include Pd and the MCM-22 type molecular sieve.

Because the alkylation and many other reactions, such as the hydrogenation reactions, taking place on the surface of the catalyst particles are exothermic, uneven distribution of the liquid and/or gas feed materials in the bed of the catalyst will result in uneven temperature distribution. In the process of the present disclosure, a substantially uniform temperature of the catalyst bed below the upper surface thereof can be achieved due to the substantially uniform distribution of the liquid and gas feed materials. As such, the actual temperature of the bed of the catalyst across one or more horizontal cross-sections below the upper surface of the bed having distance(s) from the upper surface of HH can range from $a1*Tav$ to $a2*Tav$, where Tav is the average temperature of the catalyst material across the whole given cross-section with a specific distance from the upper surface HH, and HH can be: 10.0 cm, 20.0 cm, 40.0 cm, 50.0 cm, 60.0 cm, 80.0 cm, 100 cm, 120 cm, 140 cm, 150 cm, 180 cm, 200 cm, or even larger, a1 can be 0.60, 0.65, 0.70, 0.75, 0.80, 0.85, 0.90, 0.95, 0.98, or even 0.99, and a2 can be 1.40, 1.35, 1.30, 1.25, 1.20, 1.15, 1.10, 1.05, 1.02, or even 1.01. The actual temperature of the bed of the catalyst across one or more horizontal cross-sections below the upper surface of the bed having distance(s) from the upper surface of HH can range from Tav−b1° C. to Tav+b2° C., where Tav is the average temperature of the catalyst material across the whole given cross-section with a specific distance from the upper surface HH, and HH can be: 10.0 cm, 20.0 cm, 40.0 cm, 50.0 cm, 60.0 cm, 80.0 cm, 100 cm, 120 cm, 140 cm, 150 cm, 180 cm, 200 cm, or even larger, and b1 can be 10, 9, 8, 7, 6, 5, 3, 2, or 1, and b2 can be 20, 19, 18, 17, 16, 15, 14, 13, 12, 11, 10, 9, 8, 7, 6, 5, 3, 2, or 1.

The substantially uniform distribution of the liquid and gas feed material resulting from the process of the present disclosure enables a substantially uniform molar ratio of the reactive component in the gas material to the component in the liquid reactive with the reactive component in the gas material. That ratio in one or more horizontal cross-sections below the upper surface of the bed of the catalyst having distance(s) from the upper surface of HH can range from $a1*Rav$ to $a2*Rav$, where Rav is the average ratio across the whole given cross-section with the specific distance from the upper surface HH, and HH can be: 10.0 cm, 20.0 cm, 40.0 cm, 50.0 cm, 60.0 cm, 80.0 cm, 100 cm, 120 cm, 140 cm, 150 cm, 180 cm, 200 cm, or even larger, a1 can be 0.60, 0.65, 0.70, 0.75, 0.80, 0.85, 0.90, 0.95, 0.98, or even 0.99, and a2 can be 1.40, 1.35, 1.30, 1.25, 1.20, 1.15, 1.10, 1.05, 1.02, or even 1.01.

The process of the present disclosure is particularly useful and advantageous for the hydroalkylation of benzene for making cyclohexylbenzene, as described briefly above. In this aspect, as a result of the high uniformity of the liquid distribution, temperature distribution, $H_2$ to benzene molar ratio distribution, very low concentrations of by-products such as biphenyl and bicyclohexane can be achieved in the hydroalkylation effluent. As a result of the implementation of the present invention, the hydroalkylation reaction effluent comprises biphenyl at a concentration of at most XX ppm, where XX can be: 500, 400, 300, 200, 100, 80, 60, 50, 40, 20, 10, 8, 6, and even 5. Advantageously, the quantity of biphenyl in the hydroalkylation reaction effluent is below the detection limit of typical commercial gas chromatography. The hydroalkylation effluent may comprise bi-cyclohexane at a concentration of at most YY wt %, where YY can be: 5.0, 4.0, 3.0, 2.0, 1.0, 0.8, 0.6, 0.4, 0.2, 0.1, 0.08, 0.05, 0.03, and even 0.01. Advantageously, the amount of bicyclohexane in the hydroalkylation reaction effluent can be below the detection limit of typical commercial gas chromatography.

Figure 1:
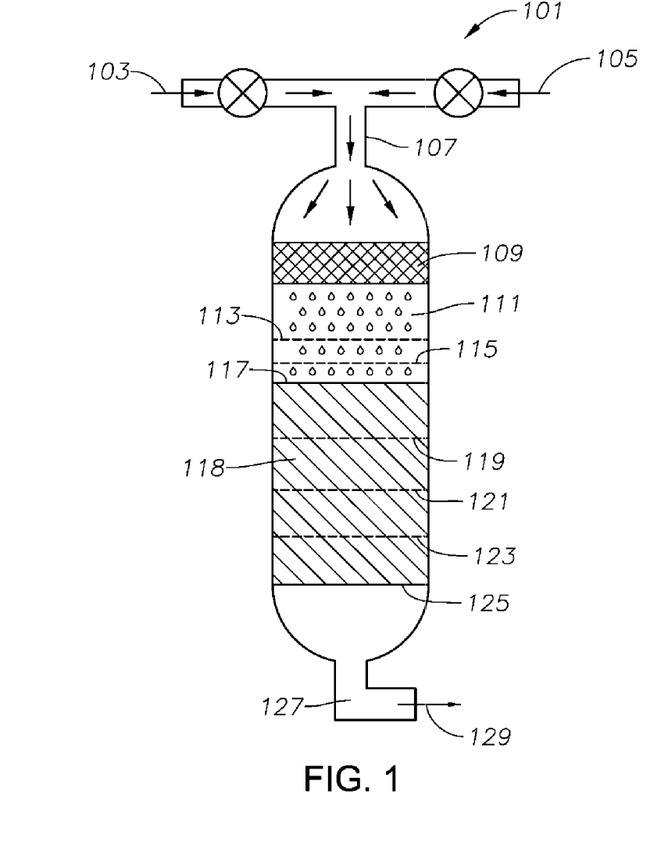
FIG. 1 is a schematic illustration of an alkylation reactor in operation according to one example of the present disclosure.

FIG. 1 schematically illustrates an reactor 101 comprising a fluid distributing device 109. In this example, a liquid feed 103 (such as a mixture comprising benzene) and a gas feed (such as a mixture comprising hydrogen gas) are mixed and pumped into the reactor 101 via a common inlet 107 at the top of the reactor 101. The fluid contacts a distributing device 109 to produce a number of liquid droplets 111 distributed substantially uniformly and an atmosphere with a substantially uniform composition in the space between the fluid distributing device 109 and the flat upper surface 117 of an alkylation/hydroalkylation catalyst bed 118. Hypothetical horizontal cross-sections 113 and 115, with a minimal distance from the upper surface 117 of the catalyst bed 118 of 2.0 cm and 1.0 cm, respectively, are illustrated. The substantially uniform distribution of the liquid droplets can be characterized by the fact that in a given period of 20.0 seconds, the number of the liquid droplets passing through any given continuous area of 10.0 cm by 10.0 cm inside 115 is within the range from 0.60 Nav to 1.40 Nav, where Nav is the arithmetic average of the number per 100 cm$^2$ of the liquid droplets passing through the whole area of cross-section 115. The substantially uniform distribution of the gas material can be indicated by a substantially uniform composition of the atmosphere inside the space defined by the hypothetical cross-sections 113 and 115 and the internal wall of the reactor. The liquid and gas, upon contacting the catalyst bed, undergo various reactions, including the alkylation reaction, as the reaction mixture travels downwards along the bed. Hypothetical horizontal cross-sections 119, 121, and 123 are taken at a depth of 1.0 cm, 10.0 cm and 50.0 cm from the upper surface 117. Due to the use of the fluid distributing device 109, the distribution of liquid across the cross-section 119 is substantially uniform. Thus, in a period of 20.0 seconds, in any given continuous area of 10.0 cm by 10.0 cm inside 119, the total quantity of liquid (or benzene) passing through is within a range from 60% to 140% of the average quantity of liquid passing through the whole cross-section 115, expressed in terms of quantity (such as weight) of the liquid per 100 cm$^2$ per second. Likewise, the distribution of liquid across the cross-sections 121 and 123 can be substantially uniform due to the use of the fluid distributing device. The alkylation reaction effluent, 129, comprising the target alkylation production, by-products and unreacted feed material, would exit the reactor at the bottom through outlet 127.

Figure 2:
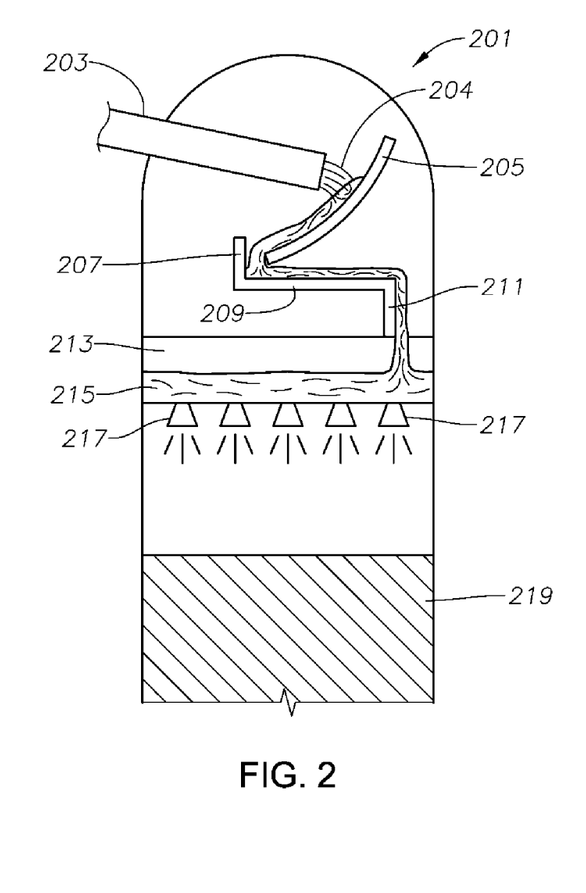
FIG. 2 is a schematic illustration of a fluid distributing device useful in another example of the processes of the present disclosure.

FIG. 2 schematically illustrates a fluid distributing device in operation in an reactor 201. In this example, a feed comprising a mixture of a liquid (e.g., one containing liquid benzene) and a gas (e.g., one containing H$_2$) is pumped into the reactor through an inlet 203, where the liquid is intercepted by a redirecting plate 205, the flow of which is further directed by a vertical dam 207, a horizontal plate 209 and a vertical channel wall 211, before the liquid 215 reaches a reservoir 213. A plurality of nozzles 217 fixed to the bottom of the reservoir 215 redistributes the liquid into the space below the reservoir 213 in the form of a number of liquid droplets, which would scatter onto the upper surface of the catalyst bed 219 substantially evenly.

Detailed description of a specific route for making phenol and/or cyclohexanone via cyclohexylbenzene made by benzene hydroalkylation is provided as follows.

Production of Cyclohexylbenzene

In the integrated process for producing phenol and cyclohexanone from benzene, the benzene is initially converted to cyclohexylbenzene by any conventional technique, including alkylation of benzene with cyclohexene in the presence of an acid catalyst, such as zeolite beta or an MCM-22 type molecular sieve, or by oxidative coupling of benzene to make biphenyl followed by hydrogenation of the biphenyl. However, in practice, the cyclohexylbenzene is desirably produced by contacting the benzene with hydrogen under hydroalkylation conditions in the presence of a hydroalkylation catalyst whereby the benzene undergoes the following Reaction-9 to produce cyclohexylbenzene (CHB):

(Reaction-9)

For an example of hydroalkylation of benzene in the presence of hydrogen for the production of cyclohexylbenzene, see U.S. Pat. Nos. 6,730,625 and 7,579,511, which are incorporated by reference. Also, see International Publications WO2009/131769 or WO2009/128984, directed to catalytic hydroalkylation of benzene in the presence of hydrogen for the production of cyclohexylbenzene. The hydroalkylation is advantageously conducted in a reactor equipped with a fluid distributing device described above.

The catalyst employed in the hydroalkylation reaction is a bifunctional catalyst comprising a molecular sieve of the MCM-22 type and a hydrogenation metal, described above.

Any known hydrogenation metal may be employed in the hydroalkylation catalyst, although suitable metals include palladium, ruthenium, nickel, zinc, tin, and cobalt, with palladium being particularly advantageous. Desirably, the amount of hydrogenation metal present in the catalyst is between 0.05 wt % and 10 wt %, such as between 0.10 wt % and 5 wt %, of the catalyst.

Suitable binder materials include synthetic or naturally occurring substances as well as inorganic materials such as clay, silica, and/or metal oxides.

Although the hydroalkylation reaction is highly selective towards cyclohexylbenzene, the effluent from the hydroalkylation reaction may contain some dialkylated products, as well as unreacted benzene and the desired monoalkylated species. The unreacted benzene may be recovered by distillation and recycled to the reactor. The lower effluent from the benzene distillation are further distilled to separate the monocyclohexylbenzene product from any dicyclohexylbenzene and other heavies. Depending on the quantity of dicyclohexylbenzene present in the reaction effluent, it may be desirable to either (a) transalkylate the dicyclohexylbenzene with additional benzene or (b) dealkylate the dicyclohexylbenzene to maximize the production of the desired monoalkylated species.

Transalkylation with additional benzene is desirably effected in a transalkylation reactor, separate from the hydroalkylation reactor, over a suitable transalkylation catalyst, such as a molecular sieve of the MCM-22 type, zeolite beta, MCM-68 (see U.S. Pat. No. 6,014,018), zeolite Y, zeolite USY, and mordenite. The transalkylation reaction is desirably conducted under at least partial liquid phase conditions, which suitably include a temperature of 100° C. to 300° C., a pressure of 800 kPa to 3500 kPa, a weight hourly space velocity of 1 hr$^{-1}$ to 10 hr$^{-1}$ on total feed, and a benzene/dicyclohexylbenzene weight ratio of 1:1 to 5:1.

Oxidation of Cyclohexylbenzene

After removal of the unreacted benzene and the polyalkylated benzenes and other heavy species, the cyclohexylbenzene is fed to the oxidation reaction.

As discussed above, the process includes oxidizing at least a portion of a feed comprising cyclohexylbenzene to produce an oxidation composition comprising cyclohexyl-1-phenyl-1-hydroperoxide. As used herein, "oxidizing" means causing an oxidation reaction to occur.

Regardless of the source or sources, a feed comprising cyclohexylbenzene may contain at least 10 wt %, or at least 25 wt %, or at least 50 wt %, or at least 65 wt %, or at least 75 wt %, or at least 95 wt %, or at least 99 wt % cyclohexylbenzene. The feed may also contain components. For example, the feed comprising cyclohexylbenzene may contain at least 1 ppm, and no greater than 1 wt % bicyclohexane, or at least 10 ppm, and no greater than 8000 ppm bicyclohexane. It may contain at least 1 ppm, and no greater than 1 wt % biphenyl, or at least 10 ppm and no greater than 8000 ppm biphenyl. It may contain at least 1 ppm and no greater than 2 wt % methylcyclopentylbenzene, or at least 10 ppm and no greater than 1 wt % methylcyclopentylbenzene as any isomer: 1-phenyl-1-methylcyclopentane, 1-phenyl-2-methylcyclopentane, and 1-phenyl-3-methylcyclopentane. There may be other components present, though desirably of low concentration, say, no greater than 1000 ppm, or no greater than 100 ppm of phenol, olefins or alkylene benzenes such as cyclohexenyl benzene, individually or in any combination. The feed comprising cyclohexylbenzene to which oxygen is introduced to cause an oxidation reaction may contain cyclohexylbenzene, any other one component, or any combination of the other components just noted in the proportions for each, or in combination just noted.

Oxidation may be accomplished by contacting an oxygen-containing gas, such as air and various derivatives of air, with the feed comprising cyclohexylbenzene.

The oxidation may be conducted in the absence or presence of a catalyst. Suitable oxidation catalysts include N-hydroxy substituted cyclic imides described in U.S. Pat. No. 6,720,462, which is incorporated herein by reference for this purpose. For example, N-hydroxyphthalimide (NHPI).

The oxidation reaction may occur under oxidation conditions. Suitable oxidation conditions include a temperature between 70° C. and 200° C., such as 90° C. to 130° C., and a pressure of 50 kPa to 10,000 kPa. A basic buffering agent may be added to react with acidic by-products that may form during the oxidation. In addition, an aqueous phase may be introduced. The reaction may take place in a batch or continuous flow fashion.

Desirably, the product of the oxidation of a feed comprising cyclohexylbenzene, i.e., the oxidation composition, contains at least 5 wt %, such as at least 10 wt %, for example, at least 15 wt %, or at least 20 wt % cyclohexyl-1-phenyl-1-hydroperoxide, based upon the total weight of the oxidation composition. In other manifestations, the oxidation composition contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation composition. The oxidation composition may further comprise imide catalyst and unreacted cyclohexylbenzene. The invention may include cyclohexylbenzene in the oxidation composition in an amount of at least 50 wt %, or at least 60 wt %, or at least 65 wt %, or at least 70 wt %, or at least 80 wt %, or at least 90 wt %, based upon total weight of the oxidation composition.

In addition, the oxidation composition may contain one or more hydroperoxides other than cyclohexyl-1-phenyl-1-hydroperoxide generated as a byproduct of the oxidation reaction of cyclohexylbenzene, or as the oxidation product of some oxidizable component other than cyclohexylbenzene that may have been contained in the cyclohexylbenzene undergoing oxidation. The reactor used for the oxidation of cyclohexylbenzene, i.e., the oxidation reactor, may be any type of reactor that allows for introduction of oxygen to cyclohexylbenzene, and may further efficaciously provide contacting of oxygen and cyclohexylbenzene to effect the oxidation reaction. For example, the oxidation reactor may comprise a simple, largely open vessel container with a distributor inlet for the oxygen-containing stream in line. The oxidation reactor may have means to withdraw and pump a portion of its contents through a suitable cooling device and return the cooled portion to the reactor, thereby managing the exothermicity of the oxidation reaction. Alternatively, cooling coils providing indirect cooling, say by cooling water, may be operated within the oxidation reactor to remove the generated heat. Alternatively, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner well known to those skilled in the art.

At least a portion of the oxidation composition may be subjected to a cleavage reaction, which may include all or some fraction of the oxidation composition as directly produced without undergoing any separation (e.g., some fraction resulting from diverting some amount of the oxidation composition as directly produced to another disposition, such as temporary storage). Thus, the at least a portion of the oxidation composition may have the same composition as the oxidation composition. Further, all or some of the oxidation composition, as directly produced, may undergo one or more separations, and an appropriate product of that separation (or separations), now modified in composition relative to the oxidation composition as directly produced, may provide the at least a portion of the oxidation composition subjected to the cleavage reaction.

For example, all or a fraction of the oxidation composition as directly produced may be subjected to high vacuum distillation, to generate a product enriched in unreacted cyclohexylbenzene relative to the oxidation composition, and the at least a portion of the oxidation composition as a residue concentrated in the desired cyclohexyl-1-phenyl-1-hydroperoxide that may be subjected to a cleavage reaction. Cyclohexylbenzene is essentially a diluent in the cleavage reaction and the neutralization reaction, and further is not a good solvent for most acid catalysts, particularly sulfuric acid. However, distinctive from the Hock process described earlier, it is convenient in the present invention that the at least a portion of the oxidation composition that will undergo the cleavage reaction be of the same composition of cyclohexylbenzene as the oxidation composition directly produced. That is to say, it is convenient that the at least a portion of the oxidation composition undergo no concentration of the hydroperoxide(s) before the acid catalyst is introduced to it, because the starting alkylbenzene cyclohexylbenzene has a significantly higher normal boiling point than the starting alkylbenzene cumene that is found in the Hock process. While within the scope of the present invention, any practical separation attempted to concentrate the cyclohexyl-1-phenyl-1-hydroperoxide or other hydroperoxides from cyclohexylbenzene prior to effecting the cleavage reaction likely requires inconvenient very low vacuum pressure distillation equipment, and even then, likely requires very high temperatures that could cause uncontrolled thermal decomposition of the hydroperoxides.

Additionally or alternatively, all or a fraction of the oxidation composition, or all or a fraction of the vacuum distillation residue may be cooled to cause crystallization of the unreacted imide oxidation catalyst, which may then be separated either by filtration or by scraping from a heat exchanger surface used to effect the crystallization, and provide an at least a portion of the oxidation composition reduced or free from imide oxidation catalyst that may be subjected to a cleavage reaction.

As another example, all or a fraction of the oxidation composition as produced may be subjected to water washing and then passage through an adsorbent, such as a 3 Å molecular sieve, to separate water and other adsorbable compounds, and provide an at least a portion of the oxidation composition with reduced water or imide content that may be subjected to a cleavage reaction. Similarly, all or a fraction of the oxidation composition may undergo a chemically or physically based adsorption, such as passage over a bed of sodium carbonate to remove the imide oxidation catalyst (e.g., NHPI) or other adsorbable components, and provide an at least a portion of the oxidation composition reduced in oxidation catalyst or other adsorbable component content that may be subjected to a cleavage reaction. Another possible separation involves contacting all or a fraction of the oxidation composition as produced with a liquid containing a base, such as an aqueous solution of an alkali metal carbonate or bicarbonate, to form an aqueous phase comprising a salt of the imide oxidation catalyst, and an organic phase reduced in imide oxidation catalyst, provided as an at least a portion of the oxidation composition that may be subjected to a cleavage reaction.

Cleavage Reaction

As discussed above, the process includes cleaving at least a portion of the oxidation composition in the presence of an acid catalyst to produce a cleavage reaction mixture comprising the acid catalyst, phenol, and cyclohexanone. As used herein, "cleaving" means causing a cleavage reaction to occur. In the cleavage reaction, at least a portion of the desired cyclohexyl-1-phenyl-1-hydroperoxide will decompose in high selectivity to cyclohexanone and phenol, and further, any other hydroperoxides present will decompose to various products, discussed below.

The acid catalyst may be at least partially soluble in the cleavage reaction mixture, stable at a temperature of at least 185° C. and has a lower volatility (higher normal boiling point) than cyclohexylbenzene. The acid catalyst may be also at least partially soluble in the treated cleavage reaction mixture.

Acid catalysts include, but are not limited to, Bronsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, and sulfur trioxide. Sulfuric acid is a preferred acid catalyst.

The cleavage reaction mixture may contain at least 50 weight-parts-per-million (ppm) and no greater than 3000 ppm of the acid catalyst, or at least 150 ppm and no greater than 2000 ppm of the acid catalyst, or at least 300 ppm and no greater than 1500 ppm of the acid catalyst, based upon total weight of the cleavage reaction mixture.

The cleavage reaction mixture may contain cyclohexylbenzene in an amount of at least 30 wt %, or at least 40 wt %, or at least 50 wt %, or at least 60 wt %, or at least 65 wt %, or at least 70 wt %, or at least 80 wt %, or at least 90 wt %, based upon total weight of the cleavage reaction mixture.

As a result of potentially high amounts of cyclohexylbenzene in the cleavage reaction mixture, considerably higher than cumene in the Hock process material undergoing a cleavage reaction, it may be convenient in the present invention to use more acid catalyst to effect the cleavage reaction than typically believed optimal in the Hock process, to at least partially overcome the insolubility of the acid in the cleavage reaction mixture. However, lower amounts of acid catalyst may be applied in the present invention, with appropriate additional cleavage reactor volume and residence time of the cleavage reaction mixture in the cleavage reactor to obtain high hydroperoxide conversion.

Suitable cleavage conditions may include a temperature of at least 20° C. and no greater than 200° C., or at least 40° C. and no greater than 120° C., and a pressure of at least 1 and no greater than 370 psig (at least 7 kPa, gauge and no greater than 2,550 kPa, gauge), or at least 14.5 psig and no greater than 145 psig (at least 100 kPa, gauge and no greater than 1,000 kPa, gauge) such that the cleavage reaction mixture is completely or predominantly in the liquid phase during the cleavage reaction.

Conversion of any hydroperoxide, such as cyclohexyl-1-phenyl-1-hydroperoxide, and conveniently all cyclohexyl-1-phenyl-1-hydroperoxide and other hydroperoxides, may be very high in the cleavage reaction, e.g., at least 90.0 wt %, or at least 95.0 wt %, or at least 98.0 wt %, or at least 99.0 wt %, or at least 99.5 wt %, or at least 99.9 wt %, or even 100 wt %, the percentage conversion based on the weight of a given specie of hydroperoxide, or of all cyclohexyl-1-phenyl-1-hydroperoxide, and other hydroperoxides present in the at least a portion of the oxidation composition undergoing the cleavage reaction. This is desirable because any hydroperoxide, even the cyclohexyl-1-phenyl-1-hydroperoxide, becomes a contaminant in the cleavage reaction mixture and treated cleavage reaction mixture, discussed below. Hydroperoxides cause undesired chemistry when decomposed under uncontrolled conditions outside the cleavage reaction, or if thermally decomposed under the conditions in a distillation column.

The major products of the cleavage reaction of cyclohexyl-1-phenyl-1-hydroperoxide are phenol and cyclohexanone, each of which may comprise 40 wt % to 60 wt %, or 45 wt % to 55 wt % of the cleavage reaction mixture, such wt % based on the weight of the cleavage reaction mixture exclusive of unreacted cyclohexylbenzene and acid catalyst.

The cleavage reaction mixture may comprise no greater than 30 wt %, or no greater than 25 wt %, or no greater than 15 wt % of phenol, or it may comprise at least 1 wt %, or at least 3 wt %, or at least 5 wt %, or at least 10 wt % phenol, based on total weight of the cleavage reaction mixture. Further, the cleavage reaction mixture may comprise no greater than 30 wt %, or no greater than 25 wt %, or no greater than 15 wt % of cyclohexanone, or it may comprise at least 1 wt %, or at least 3 wt %, or at least 5 wt %, or at least 10 wt % cyclohexanone, based on total weight of the cleavage reaction mixture.

The cleavage reaction mixture may further comprise at least 0.1 wt % and no greater than 10 wt %, or at least 0.5 wt % and no greater than 7 wt %, or at least 1 wt % and no greater than 5 wt %, or at least 1.5 wt % and no greater than 3 wt % of any one or combination of contaminant byproducts based on the total weight of the cleavage reaction mixture.

As used herein, a "contaminant" or a "contaminant byproduct" may include any unwanted hydrocarbon or oxygenated hydrocarbon component in the cleavage reaction mixture or the neutralized cleavage mixture, or any portion of either; that is anything other than phenol, cyclohexanone, and cyclohexylbenzene. They are unwanted because their presence indicates a decreased yield of desired product phenol and cyclohexanone from cyclohexylbenzene, or they cause difficulties in the separation and purification of phenol, cyclohexanone or unconverted cyclohexylbenzene, or some combination thereof. A contaminant in the cleavage reaction mixture, or the neutralized cleavage mixture, or any portion thereof may have been produced in any element of the present invention, or may have been contained in the feed comprising cyclohexylbenzene undergoing oxidation. For example, a contaminant may be present in the cleavage reaction mixture as a result of one or more of: (i) it was included with the cyclohexylbenzene (e.g., as a byproduct of production using hydroalkylation or alkylation); (ii) it was produced in oxidation of the feed comprising cyclohexylbenzene, and potentially the oxidation of an oxidizable component from (i); and/or (iii) it was produced in the cleavage reaction of at least a portion of the oxidation composition from (ii).

The reactor used to effect the cleavage reaction (i.e., the cleavage reactor) may be any type of reactor known to those skilled in the art. For example, the cleavage reactor may be a simple, largely open vessel operating in a near-continuous stirred tank reactor mode, or a simple, open length of pipe operating in a near-plug flow reactor mode. Alternatively, the cleavage reactor comprises a plurality of reactors in series, each performing a portion of the conversion reaction, optionally operating in different modes and at different conditions selected to enhance the cleavage reaction at the pertinent conversion range. The cleavage reactor may be a catalytic distillation unit.

The cleavage reactor may be operable to transport a portion of the contents through a cooling device and return the cooled portion to the cleavage reactor, thereby managing the exothermicity of the cleavage reaction. Alternatively, the reactor may be operated adiabatically. Cooling coils operating within the cleavage reactor(s) may be used to remove at least a port of the heat generated.

At least a portion of the cleavage reaction mixture may be subjected to a neutralization reaction, which may include all or some fraction of the cleavage reaction mixture as directly produced without undergoing any separation (e.g., some fraction resulting from diverting some amount of the cleavage reaction mixture as directly produced to another disposition, such as temporary storage). Thus, the at least a portion of the cleavage reaction mixture may have the same composition as the cleavage reaction mixture. Further, all or some of the cleavage reaction mixture as directly produced may undergo one or more separations, and an appropriate product of that separation (or separations), now modified in composition relative the cleavage reaction mixture as directly produced, may provide the at least a portion of the cleavage reaction mixture subjected to the neutralization reaction.

Contaminant Treatment

As discussed above, the cleavage reaction mixture may comprise one or more contaminants. The processes may further comprise contacting at least a portion of a contaminant with an acidic material to convert at least a portion of the contaminant to a converted contaminant, thereby producing a modified reaction mixture. Detailed description of the contaminant treatment process can be found, e.g., in International Publication WO2012/036822A1, the relevant content of which is incorporated herein by reference in its entirety.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam, and nylons, such as nylon-6 and nylon-6,6.

The phenol produced through the processes disclosed herein may be used, for example, to produce phenolic resins, bisphenol A, $\epsilon$-caprolactam, adipic acid, and/or plasticizers.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The contents of all references cited herein are incorporated by reference in their entirety.

Non-limiting embodiments of the processes of the present disclosure include:

E1. A process for making cyclohexylbenzene, the process comprising:

(1A) feeding a gas material comprising hydrogen gas and a liquid material comprising benzene into a hydroalkylation reactor;

(1B) distributing the liquid material to the upper surface of a bed of a solid hydroalkylating catalyst inside the hydroalkylation reactor such that in any given continuous area of 10.0 centimeters by 10.0 centimeters inside a first horizontal cross-section of the bed 1.0 centimeter below the upper surface of the bed, the average quantity of liquid benzene passing through the given continuous area per second $Qbz0$ is in a range from 60% to 140% of $Qbz1$, where $Qbz1$ is the average quantity of liquid benzene passing through the whole first horizontal cross-section, expressed in terms of quantity of liquid benzene per 100 square centimeters per second; and (1C) contacting liquid benzene and hydrogen gas with the catalyst under hydroalkylation conditions to produce a hydroalkylation reaction effluent comprising cyclohexylbenzene.

E2. The process of E1, wherein $Qbz0$ is in a range from 80% to 120% of $Qbz1$.

E3. The process of E1 or E2, wherein the distribution of liquid benzene in the bed is such that in any given continuous area of 10.0 centimeters by 10.0 centimeters inside (i) a horizontal cross-section of the bed 20.0 centimeters below the upper surface of the bed; and/or (ii) a horizontal cross-section of the bed 50.0 centimeters below the upper surface of the bed, the average quantity of liquid benzene passing through the given continuous area per second $Qbz3$ is in a range from 60% to 140% of $Qbz4$, where $Qbz4$ is the average quantity of liquid benzene passing through the whole given horizontal cross-section, expressed in terms of quantity of liquid benzene per 100 square centimeters per second.

E4. The process of E3, wherein $Qbz3$ is in a range from 80% to 120% of $Qbz4$.

E5. The process of any of E1 to E4, wherein in step (1A), at least a portion of the gas material and at least a portion of the liquid material are fed into the hydroalkylation reactor above the bed, and in step (1C), the hydroalkylation reaction effluent exits the hydroalkylation reactor at a location in proximity to the bottom of the bed.

E6. The process of any of E1 to E5, wherein in step (1B), a fluid distributing device is used between an inlet of the benzene liquid and the upper surface of the bed.

E7. The process of E6, wherein the fluid distributing device produces a plurality of liquid droplets each having a volume of at most 1.0 cubic centimeter in a space between the upper surface of the bed and the fluid distributing device, and the distribution of the liquid droplets in a second horizontal cross-section 1.0 centimeter above the upper surface of the bed is such that in any given continuous area of 10.0 centimeters by 10.0 centimeters of the second horizontal cross-section, the number of the liquid droplets passing through the given continuous area $Nav0$ is in a range from 60% to 140% of $Nav1$, where $Nav1$ is the average number of the liquid droplets passing through the whole second horizontal cross-section per 100 square centimeters, expressed in terms of number of droplets per 100 square centimeters per second.

E8. The process of E7, wherein Nav0 is in a range from 80% to 120% of Nav1.

E9. The process of any of E1 to E8, wherein the fluid distributing device distributes the gas material fed into the hydroalkylation reactor such that in any given continuous area of 10.0 centimeters by 10.0 centimeters within at least one of (i) the first horizontal cross-section of the bed; (ii) a horizontal cross-section 20.0 centimeters below the upper surface of the bed; and (iii) a horizontal cross-section 50.0 centimeters below the upper surface of the bed, the quantity of the gas material passing through the given continuous area per second Qgas0 is in a range from 60% to 140% of Qgas1, where Qgas1 is the average quantity of the gas material passing through the whole given horizontal cross-section, expressed in terms of quantity per 100 square centimeters per second.

E10. The process of E9, wherein Qgas0 is in a range from 80% to 120% of Qgas1.

E11. The process of any of E1 to E10, wherein the bed is packed such that the upper surface of the bed is flat and horizontal.

E12. The process of any of E1 to E11, wherein the bed is packed such that the distribution of a catalytically active component of the catalyst within the bed is uniform at at least one of the following locations: (i) the first horizontal cross-section; (ii) a horizontal cross-section 20.0 centimeters below the upper surface of the bed; and (iii) a horizontal cross-section 50.0 centimeters below the upper surface of the bed.

E13. The process of any of E1 to E12, wherein the distribution of the temperature of the catalyst in at least one given cross-section of (i) the first horizontal cross-section; (ii) a horizontal cross-section 20.0 centimeters below the upper surface of the bed; and (iii) a horizontal cross-section 50.0 centimeters below the upper surface of the bed is such that in any given continuous area of 10.0 centimeters by 10.0 centimeters in the given cross-section, the average temperature of the catalyst Tav0 is in a range from Tav1−10° C. to Tav1+20° C., where Tav1 is the average temperature of the catalyst across the whole given cross-section.

E14. The process of E13, wherein Tav0 is in a range from Tav1−5° C. to Tav1+10° C.

E15. The process of any of E1 to E14, wherein the catalyst comprises a solid acid component and a hydrogenating metal component.

E16. The process of E15, wherein the acid component comprises a molecular sieve of the MCM-22 type, and the hydrogenating metal component comprises of at least one metal in the Group 8, 9, or 10 of the Periodic Table of Elements.

E17. The process of any of E1 to E16, wherein the molar ratio of the hydrogen gas in the gas material to the benzene in the liquid material fed into the hydroalkylation reactor in step (1A) is in a range from 0.01 to 15.0.

E18. The process of E17, wherein the molar ratio of the hydrogen gas in the gas material to the benzene in the liquid material fed into the hydroalkylation reactor in step (1A) is in a range from 0.10 to 1.0.

E19. The process of any of E1 to E18, wherein the distribution of the ratio of hydrogen gas to benzene passing through at least one given cross-section of (i) the first horizontal cross-section; (ii) a horizontal cross-section 20.0 centimeters below the upper surface of the bed; and (iii) a horizontal cross-section 50.0 centimeters below the upper surface of the bed is such that in any given continuous area of 10.0 centimeters by 10.0 centimeters in the given cross-section, the average of the ratio Rav0 is in a range from 60% to 140% of Rav1, where Rav1 is the average of the ratio across the whole given cross-section.

E20. The process of E19, wherein Rav0 is in a range from 90% to 110% of Rav1.

E21. The process of any of E1 to E20, wherein the hydroalkylation reaction effluent comprises bi-phenyl at a concentration of at most 100 ppm, based on the total weight of the hydroalkylation reaction effluent.

E22. The process of any of E1 to E21, wherein the hydroalkylation reaction effluent comprises bi-phenyl at a concentration of at most 20 ppm, based on the total weight of the hydroalkylation reaction effluent.

E23. The process of any of E1 to E22, wherein the hydroalkylation reaction effluent comprises bicyclohexane at a concentration of at most 2.0 wt %, based on the total weight of the hydroalkylation reaction effluent.

E24. The process of any of E1 to E23, wherein the hydroalkylation reaction effluent comprises bicyclohexane at a concentration of at most 0.5 wt %, based on the total weight of the hydroalkylation reaction effluent.

E25. A process for making phenol and/or cyclohexanone, the process comprising:

(2A) producing cyclohexylbenzene according to the process of any of E1 to E24;

(2B) oxidizing at least a portion of the cyclohexylbenzene to obtain an oxidation reaction product comprising cyclohexylbenzene hydroperoxide; and (2C) cleaving at least part of the cyclohexylbenzene hydroperoxide to obtain a cleavage effluent comprising phenol and cyclohexanone.

E26. A process for alkylating an aromatic compound, the process comprising:

(3A) feeding a gas material and a liquid material comprising the aromatic compound into an alkylation reactor;

(3B) distributing the liquid to an upper surface of a bed of a solid catalyst inside the reactor such that in any given continuous area of 10.0 centimeters by 10.0 centimeters within a first horizontal cross-section of the bed 1.0 centimeter below the upper surface, the quantity of the liquid passing through the given continuous area per second is in a range from 60% to 140% of the average quantity of the liquid passing through the whole first horizontal cross-section, expressed in terms of quantity per 100 square centimeters per second; and

(3C) contacting the liquid and the gas material with the catalyst under alkylating conditions to produce an alkylation reaction effluent comprising an alkyl-substituted aromatic compound.

E27. The process of E26, wherein in step (3A), the gas material comprises hydrogen gas and/or an olefin, and the liquid material comprises at least one of benzene and a compound represented by the general formula (F-I):

(F-I)

wherein $R^1$, the same or different at each occurrence, each independently represents a linear or cyclic alkyl having from 1-10 carbon atoms, and m is an integer from 0 to 5.

E28. The process of E27, wherein the olefin is represented by the following general formula (F-II):

(F-II)

wherein R² and R³ each independently represents hydrogen or an alkyl group having from 1 to 4 carbon atoms, or R² and R³ are linked via a covalent bond to form together with the adjacent —CH=CH— linkage an optionally substituted cyclic group having from 4 to 10 carbon atoms.

E29. The process of E28 or E29, wherein the alkylation reaction effluent comprises a compound represented by the general formula (F-III):

(F-III)

where:

R¹, the same or different at each occurrence, each independently represents a linear or cyclic alkyl having from 1-10 carbon atoms;

m is an integer from 0 to 5; and

R² and R³ each independently represents hydrogen or an alkyl group having from 1 to 4 carbon atoms, or R² and R³ are linked via a covalent bond to form together with the adjacent —CH—CH₂— linkage an optionally substituted cyclic group having from 4 to 10 carbon atoms.

E30. The process of any of E26 to E29, wherein in step (3A), at least a portion of the gas material and at least a portion of the liquid material are fed into the reactor above the bed, and in step (3C), the alkylation reaction effluent exits the reactor at a location in proximity to the bottom of the bed.

E31. The process of any of E26 to E30, wherein in step (3A), at least a portion of the gas material and at least a portion of the liquid material are fed into the reactor at an identical location of the reactor.

E32. The process of any of E26 to E31, wherein in step (3B), a fluid distributing device is used between an inlet of the liquid material and the upper surface of the bed.

E33. The process of E32, wherein the fluid distributing device produces a plurality of liquid droplets each having a volume of at most 1.0 cubic centimeter in a space between the upper surface of the bed and the fluid distributing device, and the distribution of the liquid droplets in a second horizontal cross-section 1.0 centimeter above the upper surface of the bed is such that in any given continuous area of 10.0 centimeters by 10.0 centimeters of the second horizontal cross-section, the number of the liquid droplets passing through the given continuous area is in a range from 60% to 140% of the average number of the liquid droplets passing through the whole second horizontal cross-section per 100 square centimeters.

E34. The process of E32 or E33, wherein the fluid distributing device distributes the gas material fed into the reactor such that in any given continuous area of 10.0 centimeters by 10.0 centimeters within a first horizontal cross-section of the bed 1.0 centimeter above the upper surface, the quantity of the gas material passing through the given continuous area per second is in a range from 60% to 140% of the average quantity of the gas material passing through the whole first horizontal cross-section, expressed in terms of quantity per 100 square centimeters per second.

E35. The process of any of E26 to E34, wherein the bed is packed such that the upper surface of the bed is flat and horizontal.

E36. The process of any of E26 to E35, wherein the bed is packed such that the distribution of a catalytically active component of the catalyst within the bed is substantially uniform at least at one location of the following horizontal cross-sections:

the first horizontal cross-section;

a cross-section 20.0 centimeters below the upper surface of the bed; and a cross-section 50.0 centimeters below the upper surface of the bed.

E37. The process of any of E26 to E36, wherein the distribution of the temperature of the catalyst in a second horizontal cross-section of the bed 1.0 centimeter below the upper surface of the bed is such that in any given continuous area of 10.0 centimeters by 10.0 centimeters of the second horizontal cross-section, the average temperature of the catalyst is in a range from Tav−5° C. to Tav+20° C., where Tav is the average temperature of the catalyst across the whole second horizontal cross-section.

E38. The process of any of E26 to E37, wherein the catalyst comprises a solid acid.

E39. The process of E38, wherein the solid acid comprises a molecular sieve of the MCM-22 type.

E40. The process of any of E26 to E39, wherein the gas material comprises hydrogen gas, and the catalyst comprises a hydrogenating component and an alkylating component.

E41. The process of any of E26 to E40, wherein the gas material comprises hydrogen gas, the liquid material comprises benzene, the catalyst comprises a bi-functional hydroalkylation catalyst, and the alkylation reaction effluent comprises cyclohexylbenzene.

E42. The process of E41, wherein the alkylation reaction effluent comprises bi-phenyl at a concentration of at most 100 ppm, based on the total weight of the alkylation reaction effluent.

E43. The process of E26 or E42, wherein the alkylation reaction effluent comprises bicyclohexane at a concentration of at most 2.0 wt %, based on the total weight of the alkylation reaction effluent.

What is claimed is:

1. A process for making cyclohexylbenzene, the process comprising:
   (1A) feeding a gas material comprising hydrogen gas and a liquid material comprising benzene into a hydroalkylation reactor;
   (1B) distributing the liquid material to the upper surface of a bed of a solid hydroalkylating catalyst inside the hydroalkylation reactor such that in any given continuous area of 10.0 centimeters by 10.0 centimeters inside a first horizontal cross-section of the bed 1.0 centimeter below the upper surface of the bed, the average quantity of liquid benzene passing through the given continuous area per second Qbz0 is in a range from 60% to 140% of Qbz1, where Qbz1 is the average quantity of liquid benzene passing through the whole first horizontal cross-section, expressed in terms of quantity of liquid benzene per 100 square centimeters per second; and (1C) contacting liquid benzene and hydrogen gas with the catalyst under hydroalkylation conditions to produce a hydroalkylation reaction effluent comprising cyclohexylbenzene.

2. The process of claim 1, wherein Qbz0 is in a range from 80% to 120% of Qbz1.

3. The process of claim 1, wherein the distribution of liquid benzene in the bed is such that in any given continuous area of 10.0 centimeters by 10.0 centimeters inside (i) a horizontal cross-section of the bed 20.0 centimeters below the upper surface of the bed; and/or (ii) a horizontal cross-section of the bed 50.0 centimeters below the upper surface of the bed, the average quantity of liquid benzene passing through the given continuous area per second Qbz3 is in a range from 60% to 140% of Qbz4, where Qbz4 is the average quantity of liquid benzene passing through the whole given horizontal cross-section, expressed in terms of quantity of liquid benzene per 100 square centimeters per second.

4. The process of claim 3, wherein Qbz3 is in a range from 80% to 120% of Qbz4.

5. The process of claim 1, wherein in step (1A), at least a portion of the gas material and at least a portion of the liquid material are fed into the hydroalkylation reactor above the bed, and in step (1C), the hydroalkylation reaction effluent exits the hydroalkylation reactor at a location in proximity to the bottom of the bed.

6. The process of claim 1, wherein in step (1B), a fluid distributing device is used between an inlet of the benzene liquid and the upper surface of the bed.

7. The process of claim 6, wherein the fluid distributing device produces a plurality of liquid droplets each having a volume of at most 1.0 cubic centimeter in a space between the upper surface of the bed and the fluid distributing device, and the distribution of the liquid droplets in a second horizontal cross-section 1.0 centimeter above the upper surface of the bed is such that in any given continuous area of 10.0 centimeters by 10.0 centimeters of the second horizontal cross-section, the number of the liquid droplets passing through the given continuous area Nav0 is in a range from 60% to 140% of Nav1, where Nav1 is the average number of the liquid droplets passing through the whole second horizontal cross-section per 100 square centimeters, expressed in terms of number of droplets per 100 square centimeters per second.

8. The process of claim 7, wherein Nav0 is in a range from 80% to 120% of Nav1.

9. The process of claim 6, wherein the fluid distributing device distributes the gas material fed into the hydroalkylation reactor such that in any given continuous area of 10.0 centimeters by 10.0 centimeters within at least one of (i) the first horizontal cross-section of the bed, (ii) a horizontal cross-section 20.0 centimeters below the upper surface of the bed; and (iii) a horizontal cross-section 50.0 centimeters below the upper surface of the bed, the quantity of the gas material passing through the given continuous area per second Qgas0 is in a range from 60% to 140% of Qgas1, where Qgas1 is the average quantity of the gas material passing through the whole given horizontal cross-section, expressed in terms of quantity per 100 square centimeters per second.

10. The process of claim 9, wherein Qgas0 is in a range from 80% to 120% of Qgas1.

11. The process of claim 1, wherein the bed is packed such that the upper surface of the bed is flat and horizontal.

12. The process of claim 1, wherein the bed is packed such that the distribution of a catalytically active component of the catalyst within the bed is uniform at at least one of the following locations: (i) the first horizontal cross-section; (ii) a horizontal cross-section 20.0 centimeters below the upper surface of the bed; and (iii) a horizontal cross-section 50.0 centimeters below the upper surface of the bed.

13. The process of claim 1, wherein the distribution of the temperature of the catalyst in at least one given cross-section of (i) the first horizontal cross-section; (ii) a horizontal cross-section 20.0 centimeters below the upper surface of the bed; and (iii) a horizontal cross-section 50.0 centimeters below the upper surface of the bed is such that in any given continuous area of 10.0 centimeters by 10.0 centimeters in the given cross-section, the average temperature of the catalyst Tav0 is in a range from Tav1−10° C. to Tav1+20° C., where Tav1 is the average temperature of the catalyst across the whole given cross-section.

14. The process of claim 13, wherein Tav0 is in a range from Tav1−5° C. to Tav1+10° C.

15. The process of claim 1, wherein the catalyst comprises a solid acid component and a hydrogenating metal component.

16. The process of claim 15, wherein the acid component comprises a molecular sieve of the MCM-22 type, and the hydrogenating metal component comprises at least one metal in the Group 8, 9, or 10 of the Periodic Table of Elements.

17. The process of claim 1, wherein the molar ratio of the hydrogen gas in the gas material to the benzene in the liquid material fed into the hydroalkylation reactor in step (1A) is in a range from 0.01 to 15.0.

18. The process of claim 17, wherein the molar ratio of the hydrogen gas in the gas material to the benzene in the liquid material fed into the hydroalkylation reactor in step (1A) is in a range from 0.10 to 1.0.

19. The process of claim 1, wherein the distribution of the ratio of hydrogen gas to benzene passing through at least one given cross-section of (i) the first horizontal cross-section; (ii) a horizontal cross-section 20.0 centimeters below the upper surface of the bed; and (iii) a horizontal cross-section 50.0 centimeters below the upper surface of the bed is such that in any given continuous area of 10.0 centimeters by 10.0 centimeters in the given cross-section, the average of the ratio Rav0 is in a range from 60% to 140% of Rav1, where Rav1 is the average of the ratio across the whole given cross-section.

20. The process of claim 19, wherein Rav0 is in a range from 90% to 110% of Rav1.

21. The process of claim 1, wherein the hydroalkylation reaction effluent comprises bi-phenyl at a concentration of at most 100 ppm, based on the total weight of the hydroalkylation reaction effluent.

22. The process of claim 21, wherein the hydroalkylation reaction effluent comprises bi-phenyl at a concentration of at most 20 ppm, based on the total weight of the hydroalkylation reaction effluent.

23. The process of claim 1, wherein the hydroalkylation reaction effluent comprises bicyclohexane at a concentration of at most 2.0 wt %, based on the total weight of the hydroalkylation reaction effluent.

24. The process of claim 23, wherein the hydroalkylation reaction effluent comprises bicyclohexane at a concentration of at most 0.5 wt %, based on the total weight of the hydroalkylation reaction effluent.

25. A process for making phenol and/or cyclohexanone, the process comprising:
(2A) producing cyclohexylbenzene according to the process of claim 1;

(2B) oxidizing at least a portion of the cyclohexylbenzene to obtain an oxidation reaction product comprising cyclohexylbenzene hydroperoxide; and (2C) cleaving at least part of the cyclohexylbenzene hydroperoxide to obtain a cleavage effluent comprising phenol and cyclohexanone.

* * * * *